United States Patent
Umebayashi et al.

(10) Patent No.: US 7,347,914 B2
(45) Date of Patent: Mar. 25, 2008

(54) METHOD FOR PRODUCING AN ARTICLE HAVING AN ELASTIC BONDED BETWEEN TWO WEBS

(75) Inventors: Toyoshi Umebayashi, Osaka (JP); Syuhei Kurata, Kyoto (JP); Satoshi Tanaka, Osaka (JP)

(73) Assignee: Zuiko Corporation, Osaka (JP)

( * ) Notice: Subject to any disclaimer, the term of this patent is extended or adjusted under 35 U.S.C. 154(b) by 543 days.

(21) Appl. No.: 10/730,707

(22) Filed: Dec. 8, 2003

(65) Prior Publication Data

US 2004/0112508 A1   Jun. 17, 2004

(30) Foreign Application Priority Data

Dec. 13, 2002 (JP) ............................. 2002-361614
Apr. 15, 2003 (JP) ............................. 2003-109954

(51) Int. Cl.
  *B29C 65/00* (2006.01)
(52) U.S. Cl. ...................... 156/302; 156/164; 156/290; 156/163; 156/265; 156/494; 156/519; 156/259
(58) Field of Classification Search ................ 156/164, 156/163, 290, 302, 265, 494, 495, 519, 259; 604/385.29, 385.3
See application file for complete search history.

(56) References Cited

U.S. PATENT DOCUMENTS

| | | | |
|---|---|---|---|
| 3,629,039 A * | 12/1971 | Frick ........................... | 156/269 |
| 4,239,578 A * | 12/1980 | Gore ........................... | 156/361 |
| 4,297,157 A * | 10/1981 | Van Vliet ................... | 156/164 |
| 4,360,398 A | 11/1982 | Sabee | |
| 4,409,049 A * | 10/1983 | Passafiume et al. ........ | 156/164 |
| 4,543,141 A * | 9/1985 | Bradley et al. ............. | 156/164 |
| 4,720,415 A * | 1/1988 | Vander Wielen et al. ... | 428/152 |
| 4,849,049 A * | 7/1989 | Colton ........................ | 156/291 |
| 5,100,398 A * | 3/1992 | Leroy et al. ............ | 604/385.25 |
| 5,496,429 A * | 3/1996 | Hasse et al. ................ | 156/73.3 |
| 5,683,533 A | 11/1997 | Keighley et al. | |
| 5,716,478 A * | 2/1998 | Boothe et al. .............. | 156/302 |
| 6,336,922 B1 * | 1/2002 | VanGompel et al. ..... | 604/385.3 |
| 6,358,350 B1 | 3/2002 | Glaug et al. | |
| 6,447,628 B1 | 9/2002 | Couillard et al. | |
| 6,554,815 B1 * | 4/2003 | Umebayashi .......... | 604/385.27 |
| 6,979,380 B2 * | 12/2005 | Thorson et al. ............ | 156/259 |
| 2001/0025165 A1 * | 9/2001 | Shimoe ................. | 604/385.27 |
| 2002/0046802 A1 | 4/2002 | Tachibana et al. | |
| 2002/0092371 A1 | 7/2002 | Nakakado | |
| 2002/0103468 A1 | 8/2002 | Nakakado et al. | |

(Continued)

FOREIGN PATENT DOCUMENTS

DE    197 35 304 A1    2/1999

(Continued)

*Primary Examiner*—Jeff H. Aftergut
*Assistant Examiner*—Daniel McNally
(74) *Attorney, Agent, or Firm*—Renner, Otto, Boisselle & Sklar, LLP

(57) ABSTRACT

A method for producing an article of the present invention includes: a supply step of supplying a first web; a first bonding step of bonding the first web and an elastic together; a placement step of placing a second web so as to sandwich the elastic between the first web and the second web; and a second bonding step of bonding the first web, the elastic and the second web together at a plurality of locations.

16 Claims, 10 Drawing Sheets

U.S. PATENT DOCUMENTS

| | | |
|---|---|---|
| 2002/0129888 A1* | 9/2002 | Otsubo et al. ............... 156/161 |
| 2002/0138056 A1 | 9/2002 | Kuen et al. |
| 2002/0148557 A1* | 10/2002 | Heller et al. ................ 156/252 |
| 2003/0051805 A1* | 3/2003 | Mlinar et al. ............... 156/269 |
| 2003/0112999 A1* | 6/2003 | Calvert ....................... 382/111 |
| 2003/0124331 A1 | 7/2003 | Morell et al. |
| 2003/0135189 A1 | 7/2003 | Umebayashi |

FOREIGN PATENT DOCUMENTS

| | | |
|---|---|---|
| EP | 0 320 991 | 6/1989 |
| EP | 1004285 A1 * | 5/2000 |
| EP | 1 240 881 A1 | 9/2002 |
| EP | 1 350 498 A1 | 10/2003 |
| JP | 63-317576 | 12/1988 |
| JP | 07-136210 | 5/1995 |
| JP | 2001-240299 | 9/2001 |
| WO | 99/65439 | 12/1999 |
| WO | 00/37009 | 6/2000 |
| WO | 01/44086 | 6/2001 |
| WO | 03/086258 A1 | 10/2003 |

* cited by examiner

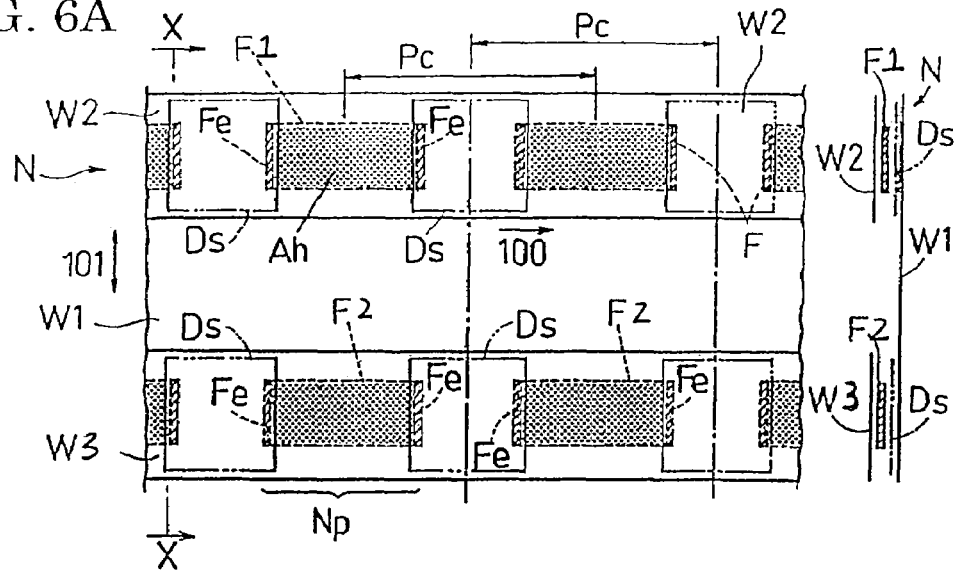
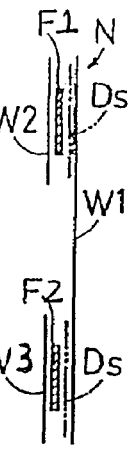
FIG. 6A
FIG. 6B
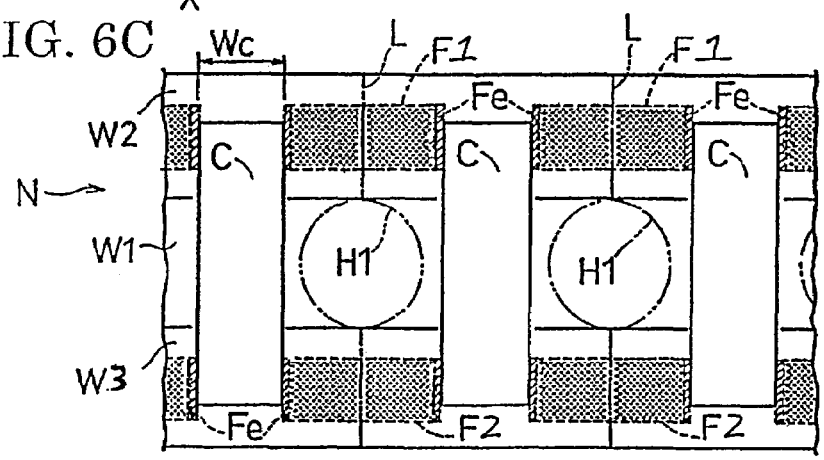
FIG. 6C
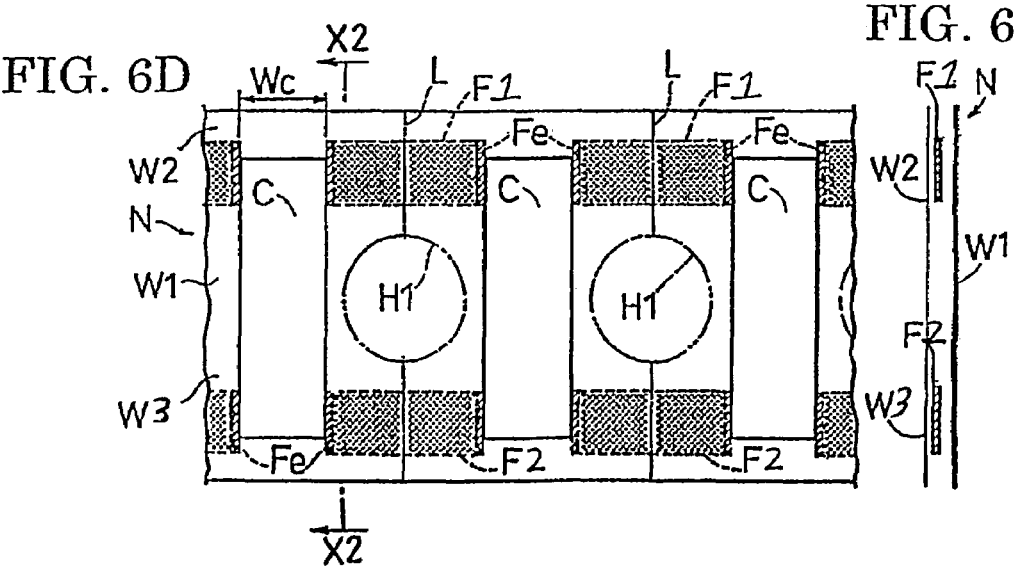
FIG. 6D
FIG. 6E

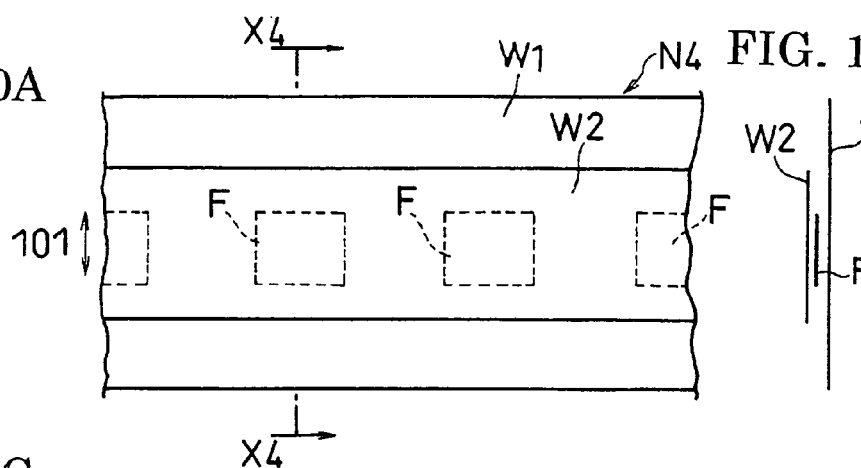
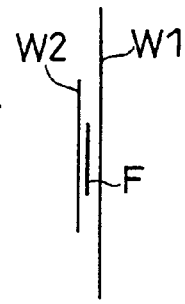
FIG. 10A
FIG. 10B
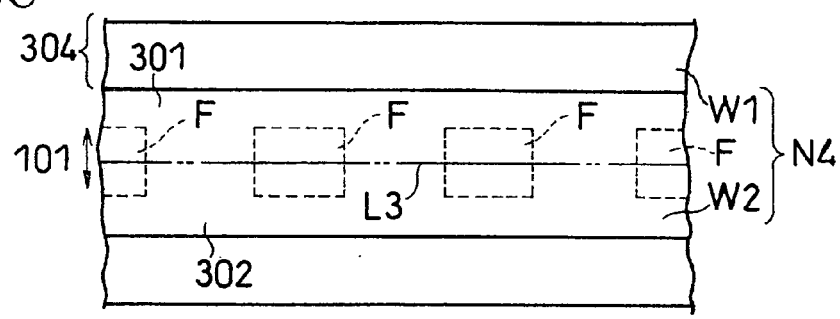
FIG. 10C
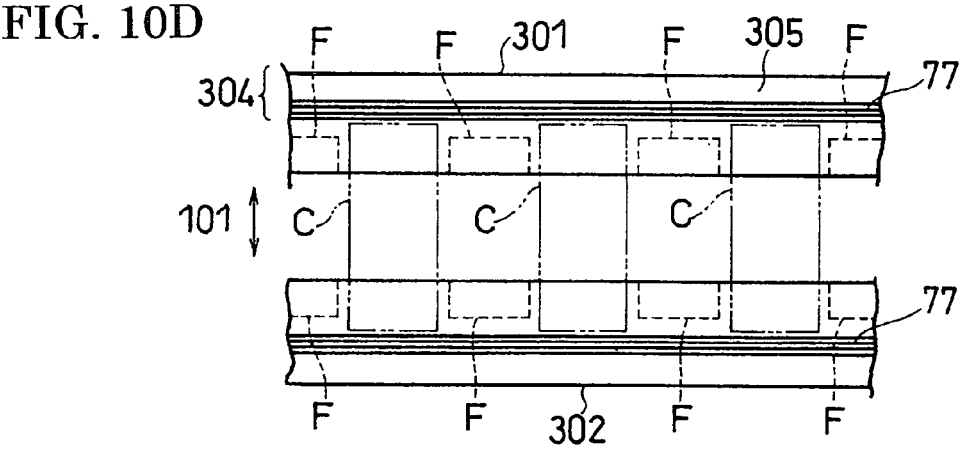
FIG. 10D
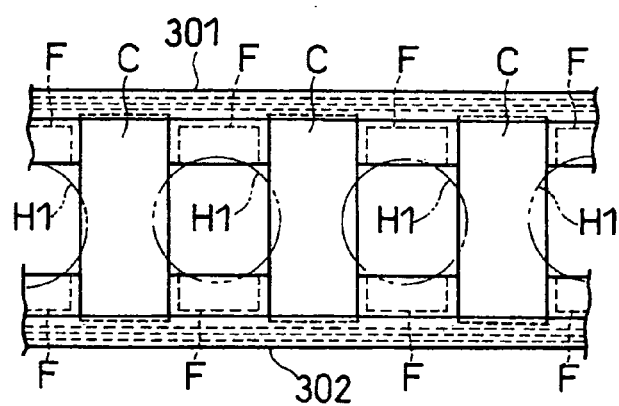
FIG. 10E

METHOD FOR PRODUCING AN ARTICLE HAVING AN ELASTIC BONDED BETWEEN TWO WEBS

BACKGROUND OF THE INVENTION

1. Field of the Invention

The present invention relates to an apparatus and method for producing an article, and more particularly to an apparatus and method for producing a worn article.

2. Description of the Related Art

Worn articles having side panels are known in the art (e.g. International Publication WO00/37009). Side panels are part of the waist portion of a diaper or a pants-type diaper, protruding sideways from the front and/or back body portions.

A diaper or a pants-type diaper having side panels is produced in a so-called "longitudinal flow" process (e.g., International Publication WO99/65439, and European Publication No. EP 0 320 991 A3). The "longitudinal flow" process is a type of production process, in which the width direction of a diaper or a pants-type diaper being produced is perpendicular to the web flow direction, as opposed to the "lateral flow" process, in which the width direction of a diaper or a pants-type diaper being produced is along the web flow direction.

However, side panels are usually costly and are difficult to produce in an in-line (lateral flow) process.

SUMMARY OF THE INVENTION

It is therefore an object of the present invention to provide an apparatus and method for producing a worn article having a member similar to a side panel in an inexpensive way and in an in-line process.

A method for producing an article of the present invention includes: a step of supplying a continuous first web; an application step of intermittently applying an adhesive on the first web or applying an adhesive on an elastic; a cutting step of cutting and dividing a continuous elastic being stretched into pieces; a first bonding step of bonding the cut-off elastics on the first web via the adhesive while the elastics are stretched; a placement step of placing a second web on the first web having the elastics bonded thereon while the elastics are stretched so that the elastics are sandwiched between the first web and the second web; and a second bonding step of thermally bonding the first web, the elastic and the second web together.

The elastics are sandwiched between the first web and the second web while being stretched. Therefore, in a laminate portion where the first web, the elastics and the second web are provided, the elastics shrink to form gathers of the worn article after the production of the worn article. Therefore, it is possible to produce an article in a so-called "lateral flow (in-line)" process without having to purchase members corresponding to side panels having elastics placed thereon in advance. The gathers may be fit gathers of the article or gathers of the side panels.

In the second bonding step, a plurality of through holes serving as vent holes may be formed by a heat embossing process in the laminate portion where the first web, the elastics and second web are provided. By forming the vent holes, it is possible to prevent the worn article from becoming stuffy when worn.

The production method may further include a placement step of placing an absorbent between adjacent ones of the elastics, which have been placed intermittently, so that no portion of the absorbent is placed on the elastics.

If the absorbent and the elastics have substantially no overlap therebetween, the absorbent having a relatively large thickness is not influenced by the shrinkage of the elastics and is thus unlikely to get stiff, thereby improving the wearability.

The elastic may be a sheet-like member (a fabric or a film, etc.). Unlike a string-like member, a sheet-like member can be bonded in a planar manner. Therefore, in the application step, a laminate member can easily be formed by applying the adhesive along the upstream edge and the downstream edge of the divided elastics. In such a case, the adhesive can be applied so that there is no adhesive in at least a portion of the elastics between these edges. Then, it is possible to reduce the stiffness of the gathers due to the presence of the adhesive.

The width of the first web may be greater than that of the elastic, and the elastics may be placed along the opposite edges of the first web (opposing each other in the width direction). Thus, by placing the elastics in a portion of the first web in the width direction, it is possible to form fit gathers by the elastics.

The first web may form the outer material of the worn article, and may be, for example, a liquid-permeable or liquid-impermeable non-woven fabric. Alternatively, the first web may be a multilayer sheet in which a design sheet having patterns thereon is placed partially or entirely across the non-woven fabric.

The second web may form the inner material of the worn article, and may be a liquid-permeable or liquid-impermeable non-woven fabric.

The elastic may be made of a rubber thread, a rubber tape, a rubber net, an elastic film, or a material including a thermoplastic elastic. A material including a thermoplastic elastic may be a hot melt resin. Moreover, an elastic film may include a plurality of holes or slits therein. The adhesive may be a hot melt resin. Note that since the first and second webs and the elastics are thermally bonded together, they may be formed from thermoplastic resin materials having a high bonding affinity to each other.

The article may be a worn article. The worn article may be a finished or semi-finished product of a sanitary napkin, a disposable diaper, disposable pants or a bandage, or may be a single-layer or multilayer sheet of woven fabric, non-woven fabric, a liquid-permeable sheet or a liquid-impermeable sheet.

BRIEF DESCRIPTION OF THE DRAWINGS

FIG. 6A illustrates a combined web N, FIG. 6B is a cross-sectional view of the combined web N of FIG. 6A taken along line X-X, FIG. 6C illustrates the combined web N having absorbents C placed thereon, FIG. 6D illustrates the combined web N in which a second web W2 is a single sheet, and FIG. 6E is a cross-sectional view of the combined web N of FIG. 6D taken along line X2-X2.

FIG. 10A illustrates a combined web N4 of still another worn article, FIG. 10B is a cross-sectional view of the combined web N4 taken along line X3-X3, FIG. 10C illustrates the combined web N4 after it is cut into two pieces by a die cutter 60, FIG. 10D illustrates the combined web N4 after it is cut into two pieces and after the two pieces are spaced apart from each other, with the absorbents C and waist elastics 77 placed thereon, and FIG. 10E illustrates the combined web N4 after trimming leg holes H1.

DESCRIPTION OF THE PREFERRED EMBODIMENTS

Preferred embodiments of the present invention will now be described with reference to the drawings.

Figure 1:
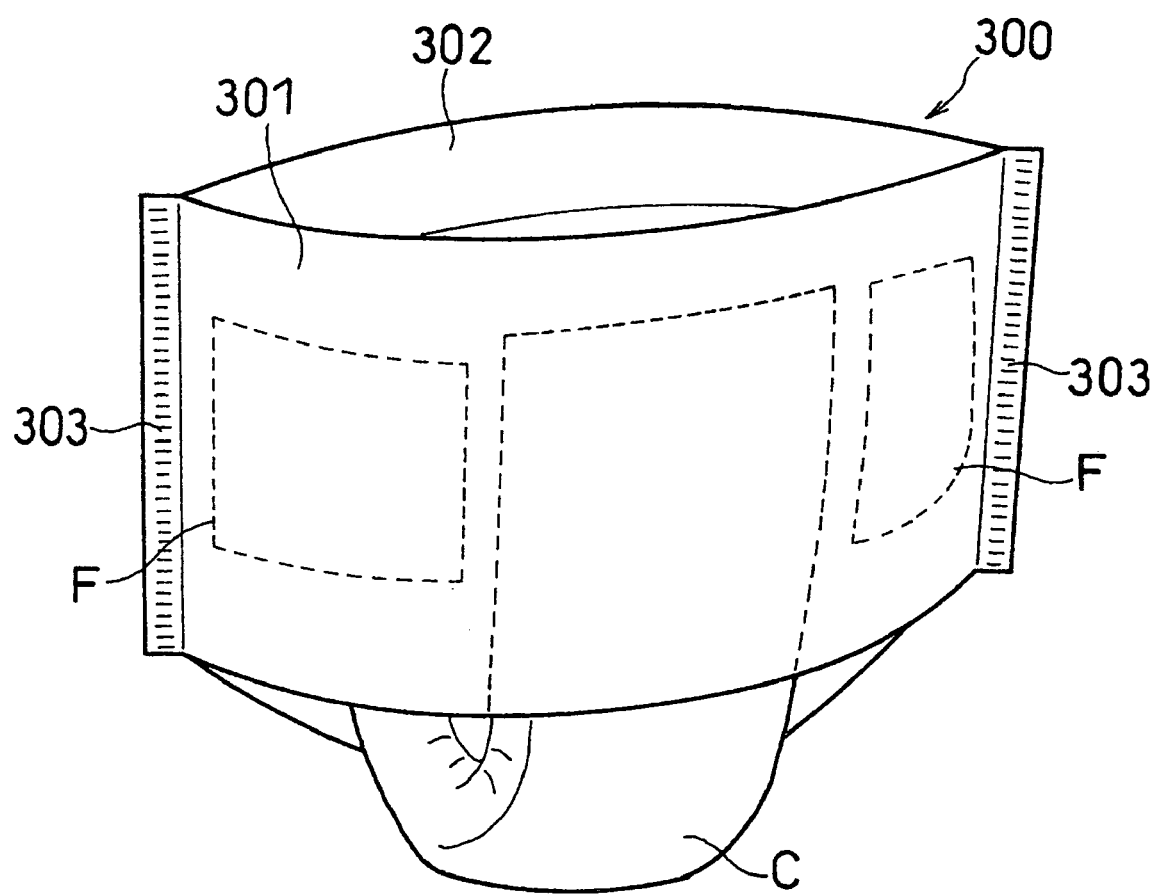
FIG. 1 illustrates an example of a worn article produced by a production apparatus or method of the present invention.

FIG. 1 illustrates an example of a worn article produced by the production apparatus or method of the present invention.

A worn article 300 includes a first waist portion 301, a second waist portion 302 and an absorbent C. The first waist portion 301 and the second waist portion 302 are connected to each other at their side edges 303. One end of the absorbent C is connected to the first waist portion 301, and the other end thereof is connected to the second waist portion 302. The absorbent C is capable of absorbing and holding body exudates of the wearer (e.g., urine or blood).

Elastics F are placed on the first waist portion 301 and the second waist portion 302. The worn article 300 fits the wearer as the elastics F shrink.

In a worn article produced by the production apparatus or method of the present invention, portions of the first waist portion 301 and the second waist portion 302 where the absorbent C is placed are not shrunk by the elastics F, thereby providing a worn article of a higher commercial value. Thus, the elastics F are basically not placed on portions of the first waist portion 301 and the second waist portion 302 where the absorbent C is placed.

The first waist portion and the second waist portion may be continuous and cover at least a portion of the absorbent. An example of an apparatus for producing a worn article in which the first waist portion and the second waist portion are integral with each other will now be described with reference to FIG. 2.

The production apparatus includes a first placement device 51, a second placement device 52, a third placement device 53, a thermal bonder 50 and an assembly station 54.

In the first placement device 51, a design sheet Ds carried by a belt 51a is sucked onto an anvil roll 51b and cut off by a cutter roll 51c, thereby placing the design sheet Ds on a first web W1. The surface of the anvil roll 51b includes a plurality of suction apertures for sucking the design sheet Ds thereonto. The suction is stopped when the design sheet Ds is placed on the first web W1. Alternatively, an air may be discharged out of the anvil roll 51b through the suction apertures so as to facilitate the separation of the design sheet Ds from the anvil roll 51b. The first placement device 51 may be a mechanism disclosed in Japanese Laid-Open Patent Publication No. 2003-237011.

The anvil roll 51b may alternatively be a repitch drum used in the second placement device 52 to be described later. Note that the first web W1 may be a non-woven fabric.

The design sheet Ds has patterns, colors, or a combination thereof. For example, the design sheet Ds may have drawings and/or characters, etc. The design sheet Ds placed on the first web W1 may have a length greater than the interval between the elastics F on the first web W1, for example, so as to conceal any poorly-finished end portions of the elastics F. Note that if a second web W2 is used as an outer material, the design sheet Ds may be placed on the second web W2. Moreover, the design sheet Ds may be optional, if patterns, colors, or a combination thereof are provided in advance on the first web W1, or in order to reduce the cost of the worn article. Thus, the production apparatus may not have the first placement device 51.

Figure 3A:
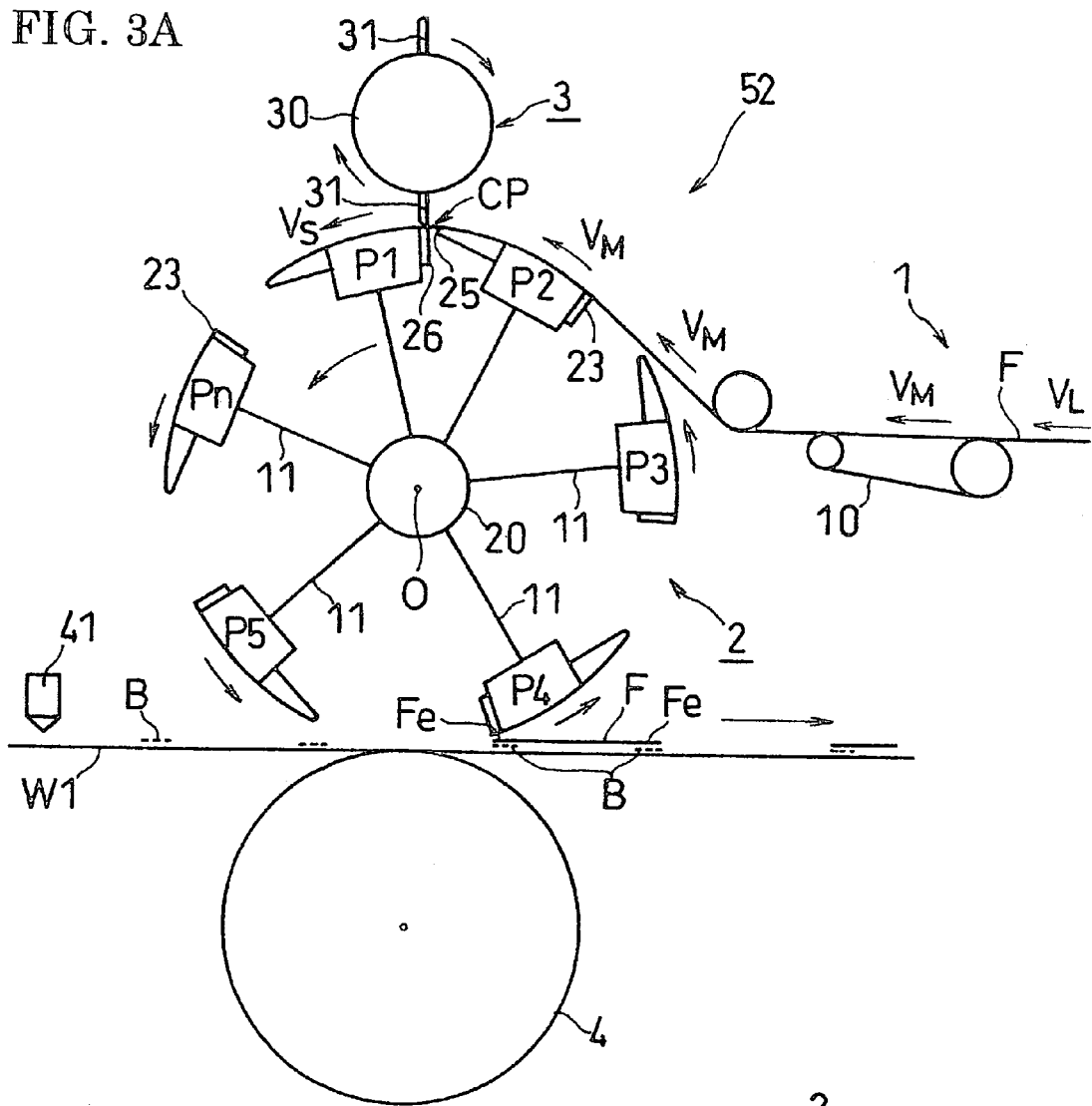
FIG. 3A is a schematic side view of a second placement device 52.
Figure 3B:
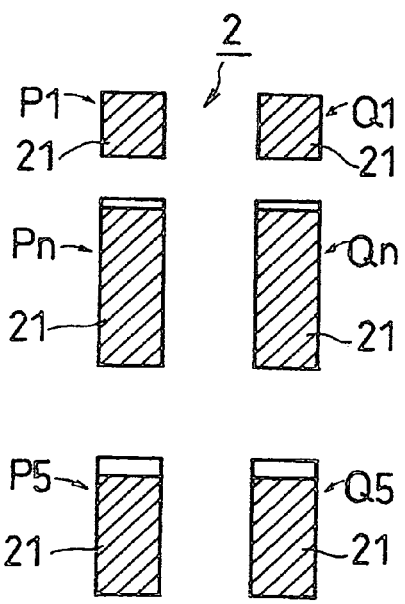
FIG. 3B is a schematic front view of a repitch drum 2 of the second placement device 52.

FIG. 3A is a schematic side view of an example of the second placement device 52. FIG. 3B is a schematic front view of a repitch drum 2 of the second placement device 52 of FIG. 3A. The second placement device 52 cuts the elastic F into pieces of a predetermined length while stretching the elastic F, and places the cut-off elastics F on the first web W1 while increasing the interval therebetween. For example, the second placement device 52 includes a supply section 1, the repitch drum 2, a cutter 3 and a transfer section 4.

The elastic F is carried downstream while being stretched by the supply section 1 to the repitch drum 2. The repitch drum 2 cuts the stretched elastic F into pieces of a predetermined length, and carries the cut-off elastics F to the transfer section 4. The transfer section 4 transfers the elastics F onto the first web W1.

The supply section 1 includes a conveyer 10 that is rotated at a medium velocity $V_M$, for example. The elastic F is carried at a low velocity $V_L$, which is lower than the medium velocity $V_M$, upstream of the conveyer 10, and is then accelerated by the conveyer 10 to the medium velocity $V_M$. Thus, the elastic F is stretched by the difference between the low velocity $V_L$ and the medium velocity $V_M$. The stretched elastic F is supplied downstream onto pads Pi.

Figure 4A:
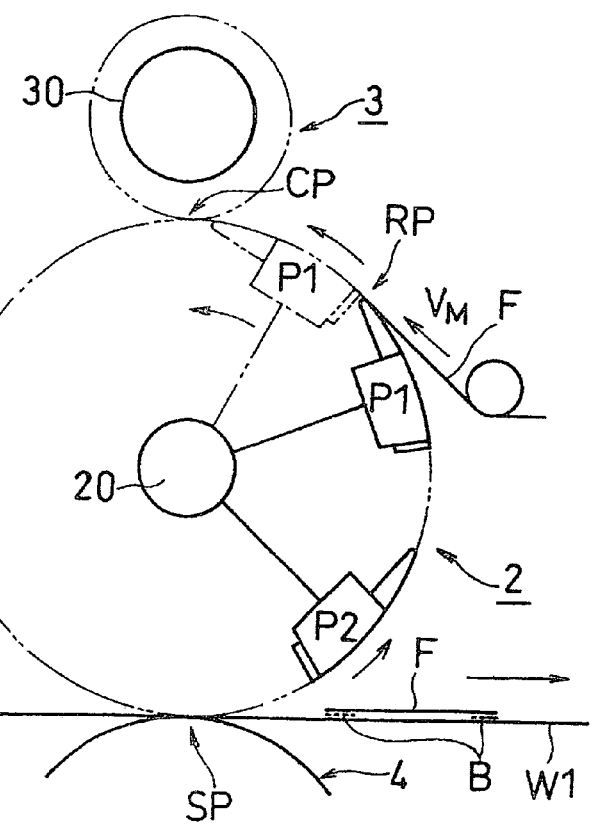
FIG. 4A illustrates a pad P1 receiving a continuous elastic F.

FIG. 4A illustrates a pad P1 receiving the continuous elastic F. The repitch drum 2 includes a plurality of pads Pi for receiving the elastic F, and receives the elastic F at the receiving position RP. After the pad P1 receives the continuous elastic F, the continuous elastic F is cut by the cutter 3 into pieces of a predetermined length.

The cutter 3 includes a cutter roll 30 and at least one blade 31 provided around the cutter roll 30. The elastic F is divided by the cutter 3 into pieces, each being carried by a pad Pi, after which the interval between two adjacent pads Pi and Pi+1 is increased, thereby increasing the interval between the cut-off elastics F (repitching the cut-off elastics F).

An anvil 23 that is contacted by the blade 31 of the cutter 3 is provided in a rear end portion 26 of the pad Pi with respect to the revolution direction of the pad Pi. As the cutter roll 30 rotates, the blade 31 contacts the anvil 23 at a predetermined time, thereby cutting off the elastic F at the cutting position CP (FIG. 3A).

The velocity of the elastic F on a pad Pi when the elastic F is cut off is preferably set to be generally equal to the circumferential velocity of the blade 31. When these velocities are different from each other, the operating lifetime of the blade 31 may be shortened. Note that if the operating lifetime of the blade 31 does not have to be taken into consideration, these velocities do not have to be matched with each other. Moreover, an anvil may be formed in a front end portion 25 of the pad Pi.

The pads Pi of the repitch drum 2 are provided around a drum 20. The repitch drum 2 may be any one of mechanisms disclosed in Japanese Laid-Open Patent Publication No. 63-317576, United States Patent Application Publication No. US2002/0103468 and United States Patent Application Publication No. US2002/0092371. Alternatively, the pads Pi may be provided and re-pitched on a conveyer, instead of on a drum.

The circumferential velocity of the pads Pi and the interval therebetween are changed by a cam mechanism, a link mechanism, or a combination thereof, for example. The structure of one pad Pi will now be described. Note that all the pads Pi perform the same operation at any particular position.

Figure 4B:
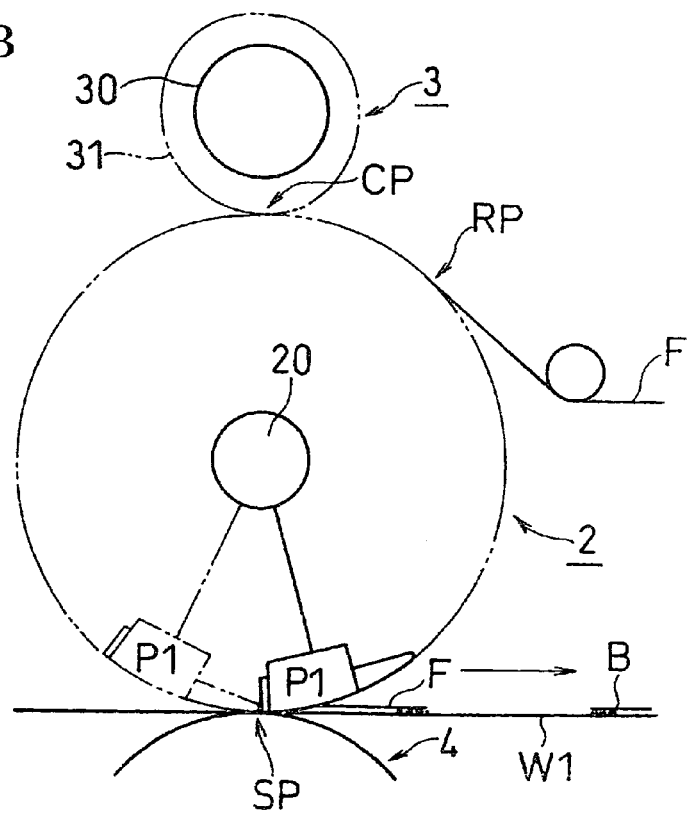
FIG. 4B illustrates the repitch drum 2 transferring the cut-off elastic F onto a first web W1 in cooperation with a transfer section 4.
Figure 5:
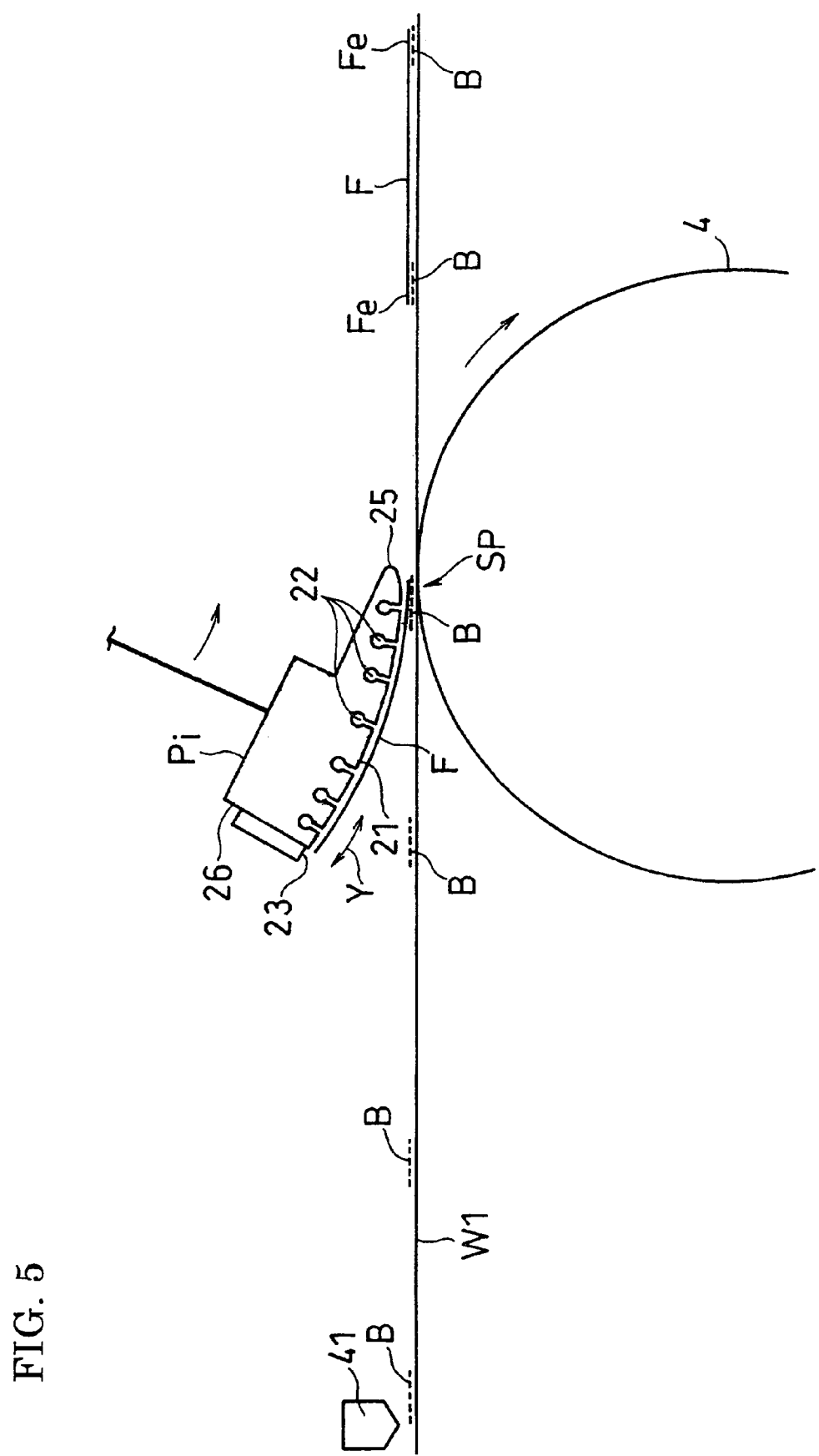
FIG. 5 is an enlarged view illustrating the transfer section 4 and the vicinity thereof.

FIG. 4B illustrates the repitch drum 2 transferring the cut-off elastic F onto the first web W1 in cooperation with the transfer section 4. FIG. 5 is an enlarged view illustrating the transfer section 4 and the vicinity thereof.

As illustrated in FIG. 5, the pad Pi includes a holding surface 21 capable of holding the elastic F thereon. The holding surface 21 is an arc-shaped surface extending in the direction Y along which the elastic F is stretched. The holding surface 21 may include a plurality of holding elements 22.

The holding elements 22 may be openings, for example. The openings are connected to an air suction source (not shown). An air is sucked through the openings at a predetermined time so that the stretched elastic F is held on the holding surface 21 when receiving the elastic F.

As the stretched elastic F is released, the air suction through the openings may be released successively from the front end portion 25 to the rear end portion 26 of the pad Pi.

Where openings are used as the holding elements 22, as the pad Pi reaches the releasing position SP, air may be discharged through the openings successively from the front end portion 25 to the rear end portion 26 so that the elastic F is gradually transferred onto the web W on the transfer section 4 starting from the front end.

Note that the holding elements 22 are preferably designed so that the holding force (suction force) is greater at the front and rear end portions 25 and 26 than in the central portion in the direction Y along which the elastic F is stretched. This is because a greater force is required near the end portions than near the central portion for holding the stretched elastic F. The uneven holding force distribution may be provided by, for example, forming more openings at the opposite end portions of the pad Pi than in the central portion thereof. In this way, the stretched elastic F can be held with a more uniform extension. Moreover, other than openings, the pad Pi may include a holding section as follows.

For example, in a case where the elastic F is a member that has minute irregularities such as urethane foam, minute irregularities may be formed on the holding surface 21 (holding section), which is hatched in FIG. 3B. Such irregularities may be obtained by bonding a member having a high friction against urethane foam (e.g., sandpaper) on the holding surface 21, or directly cutting the holding surface 21 to form irregularities.

In a case where the elastic F is a member having a smooth surface such as a film, for example, the holding surface (holding section) 21 maybe provided with a smooth surface so that the elastic F adheres to the holding surface 21. Moreover, the holding surface 21 may be made of a rubber material so that the elastic F will not slip thereon.

Furthermore, the holding elements may alternatively be provided in the form of retractable needles on the holding surface 21 of the pad Pi. For example, pad Pi may have a plurality of holes each accommodating a resilient member such as a spring therein. In such a case, one end of the resilient member may be inserted and fixed in the hole, with a needle protruding from the other end of the resilient member. The needles project from the surface of the pads Pi when receiving the elastic F so that they pierce through the elastic F to hold the stretched elastic F. In the release operation, the needles contact the transfer roll and retract into the holes, thereby releasing the elastic F. With the provision of such retractable needles, the holding section can also hold a net of elastic. In such a case, the needles are provided in the front end portion 25 and the rear end portion 26 of the first pad P1.

While the first web W1 is carried while being tangential (and in contact) with a transfer roller 40 as illustrated in FIG. 5 in the present embodiment, the first web W1 may alternatively be carried while being wound around the transfer roller 40. In either case, in order to transfer the elastic F onto the first web W1, the elastic F and the first web W1 need to be sandwiched and pressed together between the pad Pi and the transfer roller 40. Therefore, it is preferred that the circumferential velocity of the transfer roller 40 is generally equal to the moving velocity of the first web W1.

The repitch drum 2 illustrated in FIG. 3B includes two arrays of parallel pads (i.e., the pads Pi and pads Qi) spaced apart from each other, so that two lines of the elastic F can be placed on the front and back portions by the pads Pi and Qi.

When the elastic F is urethane foam, it is difficult to apply an adhesive directly on the urethane foam because the adhesive easily permeates the urethane foam, thereby failing to obtain a sufficient adhesion. In such a case, an applicator 41 may be provided upstream of the transfer roller 40, as illustrated in FIG. 5, so as to apply an adhesive B on the first web W1. In a case where the elastic F is an elastic film or an elastic non-woven fabric, an adhesive may be applied directly onto the elastic. Moreover, an adhesive may be applied on both the first web W1 and the elastic F. The bonding between the first web W1 and the elastic F may be temporary tacking.

Figure 2:
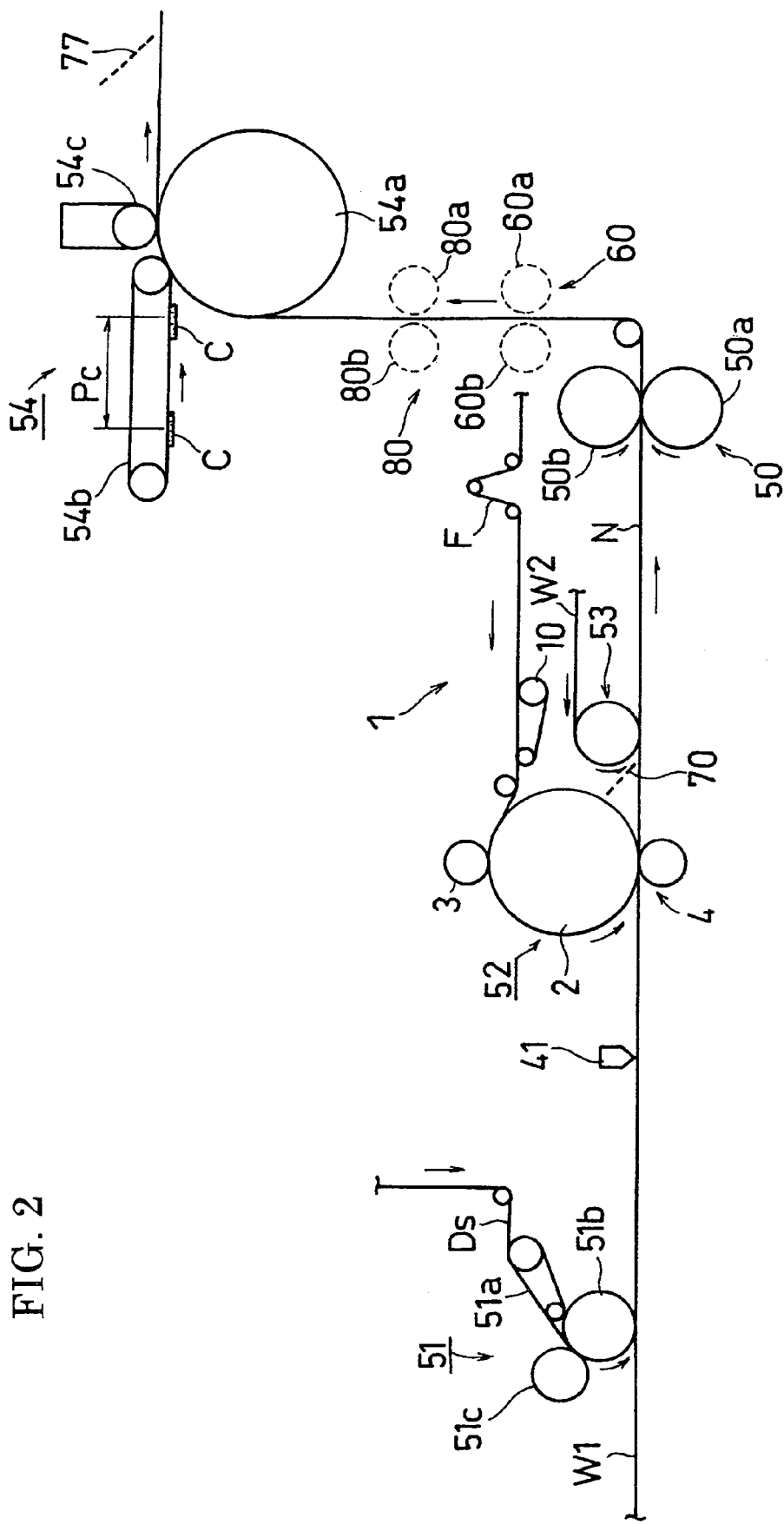
FIG. 2 illustrates an example of a production apparatus of the present invention.

The third placement device 53 illustrated in FIG. 2 further places the second web W2 on the first web W1 having the elastic F placed thereon. The second web W2 may be a non-woven fabric.

The thermal bonder 50 illustrated in FIG. 2 includes an embossing roll 50a and an anvil roll 50b. The embossing roll 50a includes a plurality of protrusions, and embosses a combined web N including the first web W1, the elastic F and the second web W2 at a plurality of locations. The first web W1, the elastic F and the second web W2 are adhered (bonded) together by an energy such as heat or vibrations from the protrusions of the embossing roll 50a. The protrusions of the embossing roll 50a may penetrate through the combined web N to form a plurality of through holes in the combined web N. Each protrusion may have a pin shape.

Moreover, the thermal bonder 50 may be a mechanism disclosed in United States Patent Application Publication No. US2002/0046802.

The assembly station 54 places the absorbents C on the combined web N. The assembly station 54 includes a transfer section 54b for transferring the absorbents C to a drum 54a, and the drum 54a for placing together the absorbents C and the combined web N. The transfer section 54b carries the absorbents C at a predetermined pitch Pc. While a belt conveyer is used for the transfer section 54b of FIG. 2, any of the mechanisms disclosed in International Publication W001/044086 and Japanese Laid-Open Patent Publication No. 2002-345889 may alternatively be used.

Moreover, the assembly station 54 may include a roll 54c as necessary for fitting the absorbents C to the combined web N.

The assembly station 54 generally places the absorbent C so as not to overlap the elastic F so that the absorbent C will not be shrunk by the elastic F. However, in order to ensure a sufficient margin for the placement of the absorbent C or to ensure a sufficient degree of freedom in designing the worn article, the absorbent C may have some overlap with the elastic F.

The absorbent C is not limited to any particular structure as long as it is capable of absorbing fluids, particularly, body exudates discharged from a human body. For example, the absorbent C may include a top sheet, a back sheet and a core sandwiched between the top sheet and the back sheet (not shown). The top sheet may be permeable to body exudates of the wearer (e.g., urine or blood). The top sheet may have a function of preventing a reverse flow of the body exudates. Alternatively, a transfer sheet may be sandwiched between the top sheet and the core for providing the function of preventing a reverse flow. The core is capable of absorbing and holding fluids. The core includes wood pulp fluff and/or a highly absorbent polymer. The core may alternatively be an airlaid material. The back sheet is impermeable to fluids. The back sheet may be a polyethylene sheet.

An example of a production method according to the embodiment of the present invention will now be described with reference to FIG. 2, FIG. 3B, FIG. 5 and FIG. 6A to FIG. 6E.

The first placement device 51 illustrated in FIG. 2 places the design sheet Ds on the externally-supplied first web W1. In the present embodiment, the design sheet Ds is placed in two locations, one on the back side and the other on the front side. Thus, the present apparatus includes two first placement devices 51. Depending on the specifications, the design sheet Ds may alternatively be placed only on the back side or the front side, or on neither side.

The adhesive B is applied on the first web W1 and/or the design sheet Ds intermittently or continuously so that the elastic F can be bonded thereto while being stretched.

The elastic F is stretched by the supply section 1 and is cut by the second placement device 52 into pieces of a predetermined length. While the adhesive B is applied in an edge portion of the area of the first web W1 and/or the design sheet Ds where the elastic F is to be placed, the adhesive B may alternatively be applied to opposite end portions of the elastic F.

In FIG. 2 and FIG. 5, the applicator 41 applies the adhesive B intermittently on predetermined areas of the first web W1. Note that the design sheet Ds placed on the first web W1 is not shown in FIG. 2 and FIG. 5. Moreover, if the application of the adhesive B does not harden the first web W1 and the elastic F (if it does not lead to a poor wearability), the adhesive B may alternatively be applied entirely across the area of the first web W1 and/or the design sheet Ds where the elastic F is to be placed, or entirely across the surface of the elastic F.

The elastic F is placed on the first web W1. The elastic F can be kept in its stretched position because of the applied adhesive B. Note that the bonding between the elastic F and the first web W1 at this point may be temporary tacking in a case where the elastic F and the first web W1 are to be bonded together by embossing, or the like, in a subsequent step.

The third placement device 53 places the second web W2 on the first web W1 having the elastic F placed thereon (FIG. 2).

FIG. 6A illustrates a semi-finished product, in which the adhesive B has been applied along the edge of the design sheet Ds, the elastic F1, F2 has been placed so as to connect adjacent design sheets Ds together, and the second web W2 has been placed so as to cover the elastic F1 and the design sheet Ds on the first web W, and the third web W3 has been placed so as to cover the elastic F2 and the design sheet Ds on the first web W1. FIG. 6B is a cross-sectional view of the semi-finished product taken along line X-X. As illustrated in FIG. 6B, the elastic F1 is sandwiched between the first web W1 and the second web W2 and the elastic F2 is sandwiched between the first web and the third web W3.

The combined web N including the first web W1, the elastic F and the second web W2 passes between the embossing roll 50a and the anvil roll 50b as illustrated in FIG. 2, where these components are thermally bonded together at a plurality of locations. The thermal bonding may be heat embossing, heat sealing, or ultrasonic bonding. When these webs and other components are bonded together, a plurality of through holes Ah are formed at least in the area where the elastic F is placed. The through holes Ah (FIG. 6A) serve as vent holes.

When more vent holes are needed, a plurality of slits may be provided in the elastic F. Slits may also be provided in the first web W1 and the elastic F or the combined web N. If slits are provided in the elastic F before it is stretched, the elastic F can be stretched more easily depending on the type of the elastic F.

The assembly station 54 places the absorbents C on the combined web N at a predetermined pitch Pc. FIG. 6C illustrates the combined web N with the absorbents C placed thereon. While the absorbent C is placed between adjacent elastics F, the absorbent C may alternatively have some overlap with the elastic F. Note that while leg holes H1 are made before the placement of the absorbents C by a die cutter 80 including a cutter roll 80a and an anvil roll 80b (shown by broken lines) in the production apparatus illustrated in FIG. 2, the leg holes H1 may alternatively be made after the placement of the absorbents C.

Then, the combined web N may be cut along the cutting line L into individual pieces of diaper-type worn articles. Alternatively, the combined web N may be cut along the cutting line L after the combined web N is folded in two and sealed near the cutting line L, thereby producing pants-type worn articles.

Note that in the worn article described above, the width of the first web W1 is greater than that of each second web W2, and the width of each second web W2 is sufficient to cover the elastic F (FIG. 6B). Alternatively, the second web W2 may be a single web having generally the same width as that of the first web W1 (FIG. 6D and FIG. 6E). A thermoplastic elastic may be used as the elastic F.

An apparatus and method for producing a worn article using a thermoplastic elastic as the elastic F will now be described with reference to FIG. 7A to FIG. 7D.

Figure 7A:
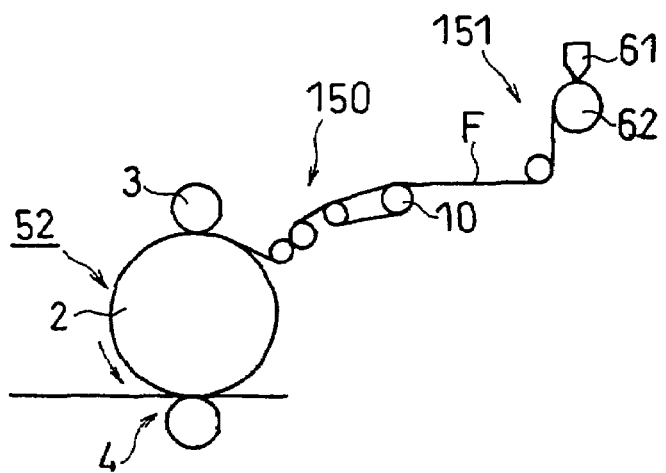
FIG. 7A illustrates the second placement device 52 and a supply section 150.

FIG. 7A illustrates the second placement device 52 and a supply section 150, which is used instead of the supply section 1 of FIG. 2. The supply section 150 includes an elastic-producing section 151 for producing the elastic F, and the conveyer 10 for stretching the elastic F. The elastic-producing section 151 includes a gun 61 for discharging a thermoplastic elastic in film, and a cooling roll 62 for cooling the discharged thermoplastic elastic for producing the elastic F.

For example, the thermoplastic elastic may be an elastic hot melt resin. The elastic hot melt resin may be a kneaded, non-volatile adhesive with no solvent, containing a thermoplastic polymer resin, a tackifier, a viscosity modifier, an antioxidant, a thermal stabilizer, a UV absorber, a filler, a plasticizer, etc. The thermoplastic polymer resin may be an elastic resin such as an olefin resin, a rubber resin, a polyamide resin, a polyester resin, or a mixture thereof. The olefin resin may be EVA (Ethylene Vinyl Acetate copolymer), APAO (Amorphous PolyAlpha Olefin), or the like. The rubber resin may be SIS (Styrene Isoprene Styrene copolymer), SBS (Styrene Butadiene Styrene copolymer), SEBS (Styrene Ethylene Butylene Styrene copolymer), SEPS (Styrene Ethylene Propylene Styrene copolymer), or the like. The composition of the kneaded material may be adjusted appropriately so that the elastic property of the thermoplastic elastic resin is optimally exerted. Moreover, the melt viscosity of the kneaded material may be adjusted so that it can be discharged from a general-purpose hot melt applicator.

Moreover, the elastic F may be a composite elastic made from a thermoplastic elastic and a web (elastic or stretchable). In such a case, the thermoplastic elastic does not have to be provided in a film pattern, but may alternatively be provided in a meshed pattern or a linear pattern (an array of straight lines). When the thermoplastic elastic is provided in a meshed pattern or a linear pattern, it maybe difficult to hold each segment separately. However, the segments of the thermoplastic elastic in the meshed or linear pattern can be held together by a web. Similarly, an elastic material such as Lycra® provided in the form of rubber threads or rubber tapes, may be attached to a web so as to produce the composite elastic.

Figure 7B:
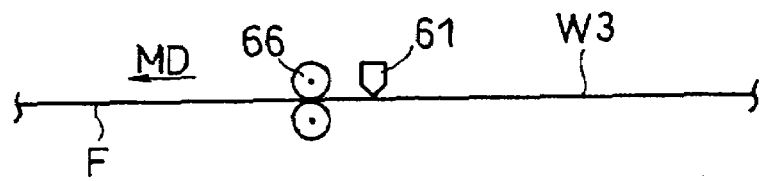
FIG. 7B to FIG. 7D illustrate different examples of an elastic-producing section 151 of the supply section 150.
Figure 7C:
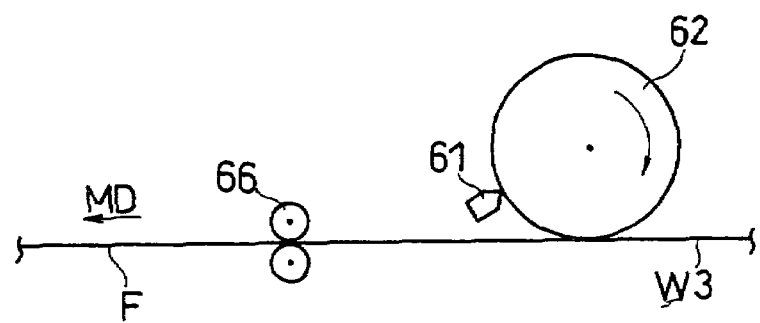
Figure 7D:
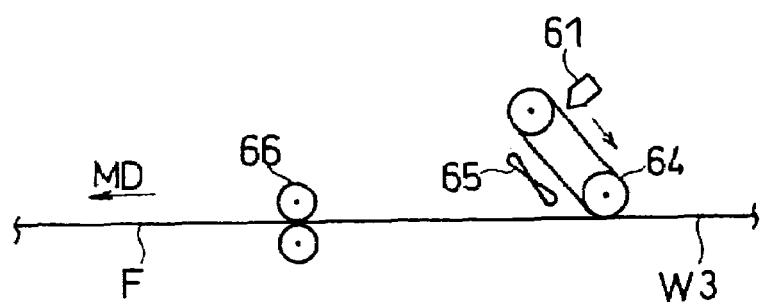

FIG. 7B to FIG. 7D illustrate different examples of the elastic-producing section 151.

In the example illustrated in FIG. 7B, the gun 61 applies a thermoplastic elastic onto a web W3, which is then nipped between nip rolls 66. In the example illustrated in FIG. 7C, the gun 61 applies a thermoplastic elastic onto the cooling roll 62, which cools the thermoplastic elastic, and then the web W3 and the cooled thermoplastic elastic are nipped between the nip rolls 66. In the example illustrated in FIG. 7D, the gun 61 applies a thermoplastic elastic onto a belt conveyer 64, which is cooled by a cooling fan 65, and then the web W3 and the cooled thermoplastic elastic are nipped between the nip rolls 66.

The gun 61 of FIG. 7B to FIG. 7D is not limited to a gun that discharges a thermoplastic elastic in a meshed pattern or a linear pattern, but may alternatively be a gun that discharges a thermoplastic elastic in a film pattern. Moreover, the roll 62 of FIG. 7A and FIG. 7C may be a chill roll.

The material of the web W3 is not limited to a synthetic fiber such as an olefin (e.g., polyethylene or polypropylene) fiber, a polyester fiber and a polyamide fiber. The material of the web W3 may alternatively be a regenerated fiber such as rayon or cuprammonium rayon, a natural fiber such as cotton, or a composite fiber such as a blend fiber or a conjugate fiber. The web W3 may have a greater extension in the flow direction, and may be obtained by any appropriate process such as a spunlace process, a spunbond process, a thermal bond process, a meltblown process, or a needle punch process. The web W3 may have an extension of 150% or more in the flow direction and have no significant extension in the width direction perpendicular to the flow direction. The web W3 may be a non-woven fabric. For example, the non-woven fabric may be a spunlace non-woven fabric Kuraray® JP4040/QR26(26GSM) manufactured by Kuraray Co., Ltd.

A method for producing another worn article will now be described with reference to FIG. 8A to FIG. 8D.

Figure 8A:
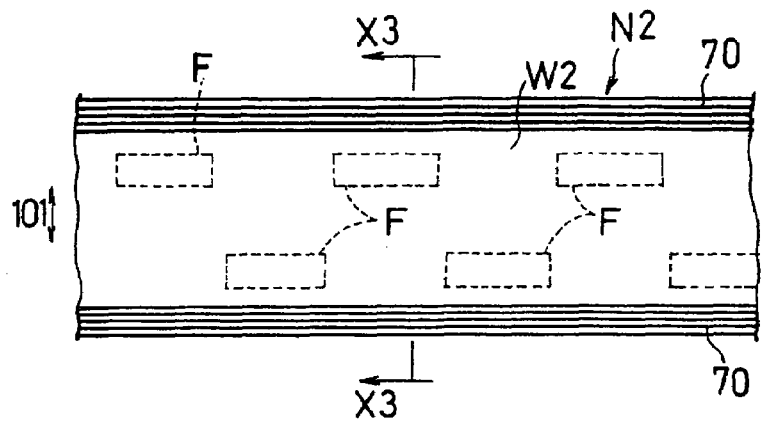
FIG. 8A illustrates a combined web N2 of another worn article.
Figure 8B:
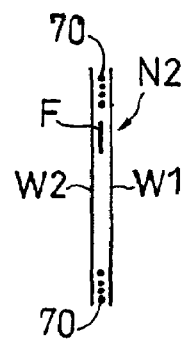
FIG. 8B is a cross-sectional view of the combined web N2 taken along line X3-X3.

FIG. 8A illustrates a semi-finished product of the worn article. In the semi-finished product, a combined web N2 includes the first web W1, two rows of elastics F alternating with each other and waist elastics 70 provided on the first web W1, and the second web W2 covering the elastics F and the waist elastics 70. FIG. 8B is a cross-sectional view of the combined web N2 taken along line X3-X3.

The elastics F sandwiched between the first web W1 and the second web W2 are placed along the opposite edges of the combined web N2 (opposing each other in a width direction 101). Moreover, the upper and lower rows of elastics F are shifted in phase from each other by half the pitch thereof.

For this arrangement, the pads Pi illustrated in FIG. 3B revolve out of phase with respect to the pads Qi. A drum for the pads Qi may be provided separately from the drum 20 for the pads Pi for achieving the out-of-phase operation. Alternatively, with only the drum 20, the pads Pi may be attached to the drum 20 at positions that are shifted by half the pitch from the positions where the pads Qi are attached to the drum 20.

Moreover, the waist elastics 70 indicated by a broken line in FIG. 2 may be sandwiched between the first web and the second web so that the finished worn article will closely fit around the waist of the wearer. This also applies to the previous embodiment.

Figure 8C:
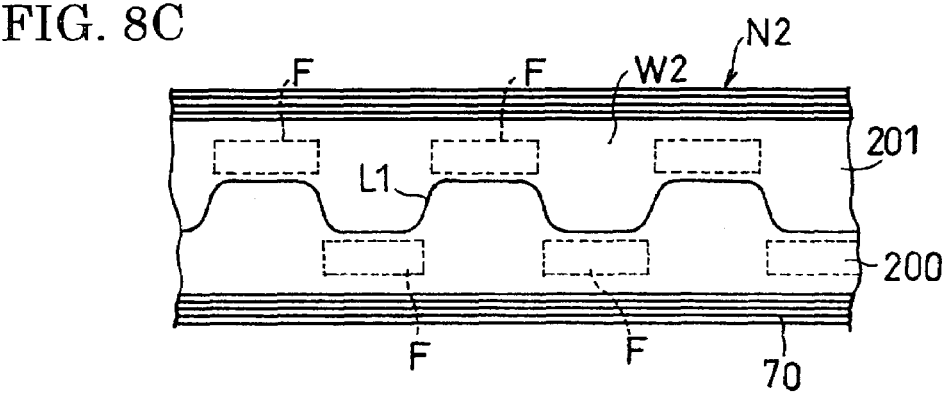
FIG. 8C illustrates the combined web N2 after it is cut into two pieces each having an alternating pattern of protruding portions and depressed portions.

FIG. 8C illustrates the combined web N2 after it is cut into two pieces each having an alternating pattern of protruding portions and depressed portions. The cutting may be done by, for example, a die cutter 60 indicated by a broken line in FIG. 2. The die cutter 60 includes a cutter roll 60a and an anvil roll 60b.

The combined web N2 is divided by the die cutter 60 into a waist portion 200 and a waist portion 201, and then the positional relationship therebetween is adjusted so that the protruding portions of the waist portion 200 and those of the waist portion 201 are in phase with each other. The phase matching can be done by using a dummy roll.

Figure 8D:
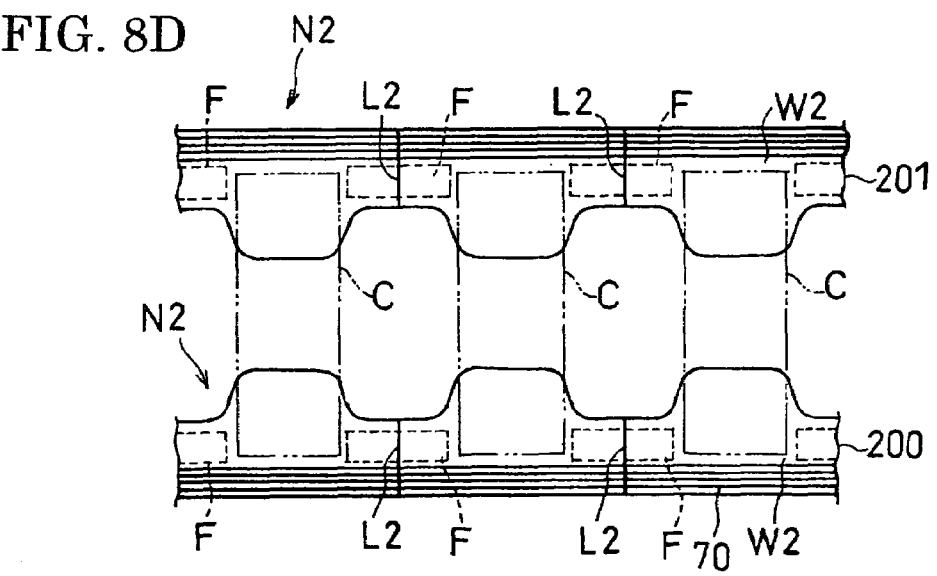
FIG. 8D illustrates the cut-off combined web N2 with the absorbents C placed thereon.

FIG. 8D illustrates the combined web N2 after the protruding portions of the waist portion 200 and those of the waist portion 201 are brought in phase with each other and after the absorbents C are placed so as to bridge between pairs of opposing protruding portions. Note that the waist portion 200 and the waist portion 201 are spaced apart from each other by a predetermined amount after cutting the combined web N2 and before placing the absorbents C.

Then, the combined web N2 (the waist portions 200 and 201) may be cut along the cutting line L2 into individual pieces of diaper-type worn articles. Alternatively, the combined web N2 may be cut along the cutting line L2 after the combined web N2 (the absorbent C) is folded in two so that the waist portion 200 and the waist portion 201 are laid over each other and sealed near the cutting line L2, thereby producing pants-type worn articles.

Figure 9A:
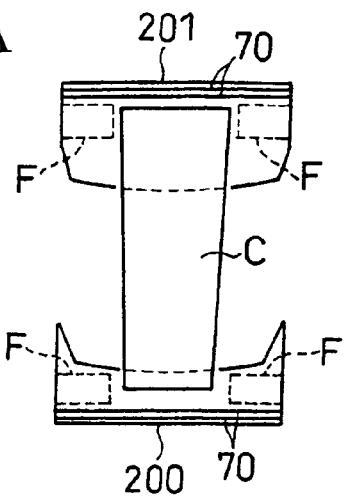
FIG. 9A illustrates an example of a worn article or a semi-finished product thereof.
Figure 9B:
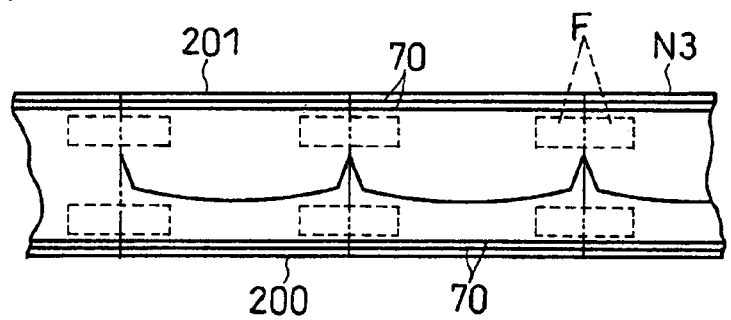
FIG. 9B illustrates a combined web N3.

Moreover, the waist portion 200 and the waist portion 201 may not need to be brought in phase with each other depending on how the combined web is cut. FIG. 9A illustrates an example of such a worn article or a semi-finished product thereof. Moreover, FIG. 9B illustrates a combined web N3 of the worn article or the semi-finished product thereof illustrated in FIG. 9A.

Figure 9C:
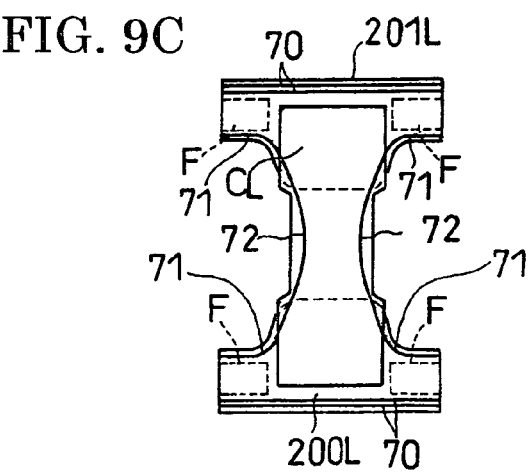
FIG. 9C illustrates an example of a worn article or a semi-finished product thereof.
Figure 9D:
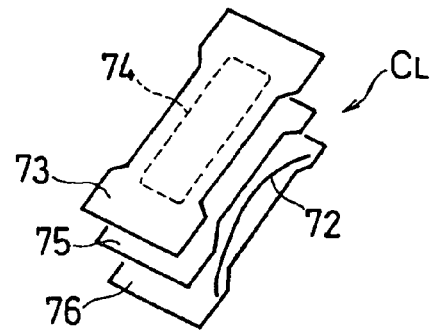
FIG. 9D illustrates an example of an absorbent CL.

Moreover, a part of the leg elastics surrounding the leg holes may be included in the waist portion of the worn article while the other part of the leg elastics is included in the absorbent. FIG. 9C illustrates an example of such a worn article or a semi-finished product thereof. Moreover, FIG. 9D illustrates an example of an absorbent CL used in the worn article or the semi-finished product thereof illustrated in FIG. 9C. A waist portion 200L, a waist portion 201L and the absorbent CL combined together provide elastics 71 and 72, which make the worn article closely fit around the legs of the wearer.

For example, the elastic 71 is provided when the second web is laid over the first web having the elastics F fixed thereon. The waist elastics 70 may also be provided in this process. The absorbent CL includes a top sheet 73, a core 74, a middle sheet 75 and a back sheet 76. The core 74 is sandwiched between the top sheet 73 and the middle sheet 75, and the elastic 72 is sandwiched between the middle sheet 75 and the back sheet 76.

The placement of the elastic 71 and the elastic 72 can be done by moving the elastic 71 or the elastic 72 in a direction across their flow directions. Any of the mechanisms disclosed in Japanese Laid-Open Patent Publication Nos. 7-136210, 2001-240299, 2003-38565, etc., may be used for arranging the elastics 71 and 72 in a curved pattern. Note that in a case where the absorbent CL does not have the middle sheet 75, the elastic 72 may be sandwiched between the top sheet 73 and the back sheet 76. Moreover, the absorbent CL, unlike the absorbent C, has the middle sheet 75, whereby it is sufficient that at least one of the middle sheet 75 and the back sheet 76 is liquid-impermeable.

An example of a method for producing still another worn article will now be described with reference to FIG. 2 and FIG. 10A to FIG. 10E.

The second placement device 52 illustrated in FIG. 2 places the stretched elastics F at a predetermined interval along the longitudinal centerline of the first web W1 (i.e., near the center of the first web W1 in the width direction 101). The third placement device 53 places the second web W2 thereon. The elastics F have a width that is greater than that of the elastics F placed on the front or back side of the combined web N of FIG. 6A. This is because each elastic F will later be divided into two pieces, one on the back side and the other on the front side. FIG. 10A illustrates a combined web N4. FIG. 10B is a cross-sectional view of the combined web N4 taken along line X4-X4.

The first web W1, the elastic F and the second web W2 are bonded together by the thermal bonder 50 illustrated in FIG. 2. Then, the combined web N4 is cut by the die cutter 60 into waist portions 301 and 302. FIG. 10C illustrates the combined web N4 after it is cut by the die cutter 60.

The waist portions 301 and 302 are spaced apart from each other by a predetermined amount in the width direction, and the absorbents C are provided so as to bridge between the waist portions 301 and 302. Specifically, one end of each absorbent C is connected to the waist portion 301, and the other end to the waist portion 302.

Moreover, as illustrated in FIG. 10D, elastics 77 are placed along opposing edges 304 of the first web W1 except for a folding margin 305. After the elastics 77 are placed, the folding margin 305 is folded back to cover the elastics 77 therein. End portions of the absorbents C may also be covered in this process.

Depending on the specifications, portions of the waist portions 301 and 302 and the absorbents C may be cut off to trim the leg holes H1, as illustrated in FIG. 10E. The leg holes H1 may be trimmed by the die cutter 80 indicated by a broken line in FIG. 2.

A production method of the present invention does not necessarily require the step of placing waist elastics, as illustrated in FIG. 6A. This is not to deny the possible advantages obtained by placing waist elastics on a worn article. For example, in the production method of the present invention, waist elastics may be sandwiched between the first web W1 and the second web W2 as illustrated in FIG. 8A, or waist elastics may be placed on the first web W1, after which the first web W1 is folded back to cover the waist elastics as illustrated in FIG. 10D. Moreover, in the production method of the present invention, waist elastics can be placed by any other suitable method known in the art.

According to the present invention, it is possible to produce a worn article similar to a worn article having side panels in an in-line (lateral flow) process. Therefore, it is possible to form gathers of a worn article without having to purchase expensive side panels having elastics placed thereon in advance. Therefore, it is possible to reduce the production cost.

What is claimed is:

1. A method for producing an article, comprising:
    as part of a lateral flow process, the steps of forming elastics for side panel-like members via the steps of:
    a supply step of supplying an elastic material;
    a separating step of cutting pieces of elastic from the elastic material when the elastic material is in a stretched state;
    a changing step of changing the interval between two adjacent pieces of elastic while the pieces are maintained in the stretched state;
    a supply step of supplying a first web;
    a transferring step of transferring the elastic pieces to the first web at the changed interval in a flow direction of the first web;
    a first bonding step of bonding the first web and the elastic pieces together;
    a placement step of placing a second web so as to sandwich the elastic pieces between the first web and the second web; and
    a second bonding step of bonding the first web, the elastic pieces and the second web together at a plurality of locations; and
    a placement step of placing an absorbent correspondingly to the interval between adjacent pieces of elastic, the adjacent pieces of elastic thereby forming the side panel-like members on each side of the absorbent.

2. A method for producing an article according to claim 1, comprising:
    cutting a combined web produced in the second bonding step into a first combined web and a second combined web;
    spacing apart the first combined web and the second combined web from each other; and
    placing the absorbent so as to bridge between the first combined web and the second combined web, which have been spaced apart from each other.

3. A method for producing an article according to claim 2, further comprising a step of making a hole for trimming a leg hole.

4. A method for producing an article according to claim 1, wherein the first bonding step comprises a step of applying an adhesive on the first web for temporarily tacking the elastic on the first web.

5. A method for producing an article according to claim 1, wherein the first bonding step comprises a step of applying an adhesive on the elastic for temporarily tacking the elastic on the first web.

6. A method for producing an article according to claim 1, wherein the second bonding step is performed by passing the first web, the elastic and the second web between an embossing roll and an anvil roll.

7. A method for producing an article according to claim 1, wherein the changing step includes changing the spacing between adjacent elastic pieces while rotating the elastic pieces about a same radius.

8. A method for producing an article, comprising:
as part of a lateral flow process, the steps of forming elastics for side panel-like members via the steps of:
a supply step of supplying an elastic material;
a separating step of cutting pieces of elastic from the elastic material when the elastic material is in a stretched state;
a changing step of changing the interval between two adjacent pieces of elastic while the pieces are maintained in the stretched state;
a supply step of supplying a first web;
a transferring step of transferring a first and second elastic piece to the first web in a flow direction of the first web;
a first bonding step of bonding the first web with first and second pieces of elastic;
a placement step of placing a second web so that the first elastic piece and the second elastic piece are sandwiched between the first web and the second web; and
a second bonding step of bonding the first web, the first and second pieces of elastic and the second web together at a plurality of; and
a placement step of placing an absorbent correspondingly to the interval between adjacent first and second elastic pieces, the adjacent pieces of elastic thereby forming the side panel-like members on each side of the absorbent.

9. A method for producing an article according to claim 8, further comprising a step of placing an absorbent.

10. A method for producing an article according to claim 8, wherein the changing step includes changing the spacing between adjacent elastic pieces while rotating the elastic pieces about a same radius.

11. A method for producing an article, comprising:
a supply step of supplying an elastic material;
a separating step of cutting pieces of elastic from the elastic material when the elastic material is in a stretched state;
a changing step of changing the interval between two adjacent pieces of elastic while the pieces are maintained in the stretched state;
a supply step of supplying a first web;
a transferring step of transferring an elastic piece to the first web in a flow direction of the first web;
a first bonding step of bonding the first web with first and second pieces of elastic;
a placing step of placing a second web so that the first elastic piece is sandwiched between the first web and the second web and placing a third web so that the second elastic piece is sandwiched between the first web and the third web; and a second bonding step of bonding the first web, the first elastic piece and the second web together at a plurality of locations and bonding the first web, the second elastic piece and the third web together at a plurality of locations;
wherein the steps are performed as part of a lateral flow process.

12. A method for producing an article according to claim 11, further comprising a step of placing an absorbent.

13. A method for producing an article according to claim 8, wherein the changing step includes changing the spacing between adjacent elastic pieces while rotating the elastic pieces about a same radius.

14. A method for producing an article, comprising the steps:
supplying a first web;
supplying first and second elastics being in a stretched state;
cutting the first and second elastics into a plurality of first stretched sheets and a plurality of second stretched sheets;
a first changing step of changing the interval between two adjacent pieces of first stretched sheets after the pieces are cut and while the pieces are maintained in the stretched state;
placing the first stretched sheets at a predetermined interval in a flow direction of the first web along one edge of the first web;
a second changing step of changing the interval between two adjacent pieces of second stretched sheets after the pieces are cut and while the pieces are maintained in the stretched state;
placing the second stretched sheets at a predetermined interval in a flow direction of the first web along the other edge of the first web;
placing a second web so as to cover the first and second stretched sheets;
thermally bonding the first and second stretched sheets between the first web and the second web to produce a laminate;
placing one end of an absorbent between two adjacent ones of the first stretched sheets;
placing the other end of the absorbent between two adjacent ones of the second stretched sheets.

15. A method for producing an article according to claim 14, wherein the first and second changing steps include changing the spacing between adjacent elastic pieces while rotating the elastic pieces about a same radius.

16. A method for producing a worn article, comprising the steps of:
supplying a first web;
supplying a stretched elastic;
cutting the elastic into a plurality of stretched sheets;
placing the sheets at a predetermined interval in a flow direction of the first web along a longitudinal centerline of the first web;
placing a second web so as to cover the sheets;
thermally bonding the first web, the sheets and the second web together to produce a laminate;
cutting the laminate, including the sheets therein, into two waist portions each being a continuous portion;
spacing apart the two waist portions from each other in a width direction of the first web;
placing one end of an absorbent on one of the waist portions; and
placing the other end of the absorbent on the other one of the waist portions.

* * * * *